US006410314B1

(12) United States Patent
Baiker et al.

(10) Patent No.: US 6,410,314 B1
(45) Date of Patent: Jun. 25, 2002

(54) EPISOMALLY REPLICATING VECTOR, ITS PREPARATION AND USE

(75) Inventors: Armin Baiker, Lauffen/Neckar; Jürgen Bode, Schoppenstedt; Christian Fetzer, München; Hans-Joachim Lipps, Tübingen; Christoph Piechaczek, Münster, all of (DE)

(73) Assignee: MultiGene Biotech GmbH Biozentrum am Hubland, Wurzburg (DE)

( * ) Notice: Subject to any disclaimer, the term of this patent is extended or adjusted under 35 U.S.C. 154(b) by 0 days.

(21) Appl. No.: 09/412,825

(22) Filed: Oct. 5, 1999

(30) Foreign Application Priority Data

Oct. 17, 1998 (DE) ......................... 198 48 017

(51) Int. Cl.⁷ .......................... C12N 15/00; C12N 15/64
(52) U.S. Cl. .................................... 435/320.1; 435/91.4
(58) Field of Search ............................. 435/320.1, 69.1, 435/69.7, 70.3; 514/44, 2; 536/23.4

(56) References Cited

U.S. PATENT DOCUMENTS 5,624,820 A * 4/1997 Cooper ....................... 435/69.1
5,985,607 A * 11/1999 Delcuve et al. ............. 435/69.1
6,030,956 A * 2/2000 Boulikas ...................... 514/44

OTHER PUBLICATIONS

Poljak et. al.; SARs stimulate but do not confer position independent gene expression, 1994, Nucleic Acids Research vol. 22, No. 22:4386–4394.*
Li et. al.; Simian Virus 40 DNA Replication In Vitro: Specificity of Initiation and Evidence for Bidirectional Replication, 1985, Molecular and Cellular Biology: 1238–1246.*
Rakusanova et. al.; Effect of Mitomycin C and Co Irradiation on the Replication of SV40 in Cell of Varying Permissivity for SV40 Replication, 1979J. Gen Virol 43: 235–239.*
Kalos et. al.; Position–Independent Transgene EXpression Mediated by Boundary Elements from the Apolipoprotein B Chromatin Domain, 1995, Molecular and Cellular Biology: 198–207.*
Schubeler et. al.; Scaffold/Matrix–Attached Regions Act upon Transcription in a Context–Dependent Manner, 1996, Biochemistry 35: 11160–11169.*
Chattopadhyay et. al.; A Nuclear Matrix Attachment Region Upstream of the T Cell Receptor B Gene Enhancer Binds Cux/CDP and SATB1 and Modulates Enhancer–dependent Reporter Gene Expression but Not Endogenous Gene expression, 1998, The Journal of Biological.*

Kohwi–Shigematsu et. al.; A Thymocyte Factor SATBI Suppresses Transcription of Stably Integrated Matrix–Attachment Region—Linked Genes, 1997; Biochemistry 36: 12005–12010.*
Piechaczek et. al.; A vector based on the SV40 origin of replication and chromosomal S/MARs replicates episomally in CHO cells; 1999, Nucleic Acids Research vol. 27, No. 2:426–428.*
Anderson; Human gene therapy; 1998, Nature vol. 392:25–30.*
Verma et. al.; Gene therapy–priomises, problems and prospects, 1997, Nature vol. 389: 239–242.*
Zabner; Cationic lipids used in gene transfer, 1997, Advanced Drug Delivery Reviews, 27:17–28.*
Zabner et. al.; Cellular and Molecular Barriers to Gene Transfer by a Cationic Lipid, 1995, The Journal of Biological Chemistry, vol. 270: 18997–19007.*
Lechardeur et. al.; Metaboloc instability of plasmid DNA in the cytosol: a potential barrier to gene transfer, 1999, Gene Therapy 6: 482–497.*
Chu et. al.; Retrovirus—mediated gene transfer into human hematopoietic stem cells, 1998, J Moi Med 76: 184–192.*
Havenga et. al.; Retroviral Stem Cell Gene Therapy, 1997, Stem Cells 15: 162–179.*
Cooper et. al.; Safety–modified episomal vectors for human gene therapy; 1997, Proc. Natl. Acad. Sci. vol. 94: 6450–6455.*
Klehr et. al.; Scaffold–Attached Regions from the Human Interferon B Domain Can Be Used To Enhance the Stable Expression of Genes under the Control of Various Promoters, 1991, American Chemical Society 1264–1270.*
www.clontech.com; pGFP–C1.*
Voet, et al.. In Biochemistry, 1990. John Wiley & Sons, New York, pp. 133–134.*
Eck, et al., 1996. In Goodman & Gilman's The pharmacological Basis of Therapeutics, Ninth Edition. McGraw–Hill, New York, pp. 77–101.*
Cossons, et al., Dec. 15, 1997. Journal of Cellular Biochemistry, 67:439–450.*
Bode, et al., 1992. Science 255:195–7.*
Scala, et al., 1990. J Exp Med, vol. 172, pp. 61–68.*
Kirinaka, et al., 1994. Appl Microbiol Biotech 41:591–6.*

* cited by examiner

Primary Examiner—Deborah Crouch
Assistant Examiner—Joseph T. Woitach
(74) Attorney, Agent, or Firm—Clark & Elbing LLP

(57) ABSTRACT

The present invention relates to stably episomally replicating vectors, comprising at least one scaffold/matrix attached region (S/MAR) and at least one viral or eukaryotic origin of replication (ORI), cells comprising these, processes for their preparation, and their use, in particular as a medicament or diagnostic.

26 Claims, 4 Drawing Sheets

Plasmid pTZ-E20

Human Interferon β gene 5' SAR : 2.2 kb EcoRI 213 - EcoRI 2413

S/MAR in pEPI-1: 2.0 kb Bgl II 429 - EcoRI 2413

SEQUENCE LISTING

<160> NUMBER OF SEQ ID NOS: 1

<210> SEQ ID NO 1
<211> LENGTH: 2206
<212> TYPE: DNA
<213> ORGANISM: Homo sapien

<400> SEQUENCE: 1

```
gaattcagca aggtcgccac gcacaagatc aatattaaca atcagtcatc t ctctttagc    60 aataaaaagg tgaaaatta  cattttaaaa atgacaccat agacgatgta t gaaaataat   120 ctacttggaa ataaatctag gcaaagaagt gcaagactgt tacccagaaa a cttacaaat   180 tgtaaatgag aggttagtga agatttaaat gaatgaagat ctaaataaac t tataaattg   240 tgagagaaat taatgaatgt ctaagttaat gcagaaacgg agagacatac t atattcatg   300 aactaaaaga cttaatattg tgaaggtata ctttctttc  acataaattt g tagtcaata   360 tgttcacccc aaaaaagctg tttgttaact tgtcaacctc atttcaaaat g tatatagaa   420
```

-continued

```
agcccaaaga caataacaaa aatattcttg tagaacaaaa tgggaaagaa t gttccacta      480 aatatcaaga tttagagcaa agcatgagat gtgtggggat agacagtgag g ctgataaaa      540 tagagtagag ctcagaaaca gacccattga tatatgtaag tgacctatga a aaaaatatg      600 gcattttaca atgggaaaat gatgatcttt ttctttttta gaaaaacagg g aaatatatt      660 tatatgtaaa aaataaaagg gaacccatat gtcataccat acacacaaaa a aattccagt      720 gaattataag tctaaatgga gaaggcaaaa ctttaaatct tttagaaaat a atatagaag      780 catgccatca tgacttcagt gtagagaaaa atttcttatg actcaaagtc c taaccacaa      840 agaaaagatt gttaattaga ttgcatgaat attaagactt attttttaaaa t taaaaaacc      900 attaagaaaa gtcaggccat agaatgacag aaaatatttg caacacccca g taagagaa      960 ttgtaatatg cagattataa aaagaagtct tacaaatcag taaaaaataa a actagacaa     1020 aaatttgaac agatgaaaga gaaactctaa ataatcatta cacatgagaa a ctcaatctc     1080 agaaatcaga gaactatcat tgcatataca ctaaattaga gaaatattaa a aggctaagt     1140 aacatctgtg gcaatattga tggtatataa ccttgatatg atgtgatgag a acagtactt     1200 taccccatgg gcttcctccc caaaccctta ccccagtata aatcatgaca a atatacttt     1260 aaaaaccatt accctatatc taaccagtac tcctcaaaac tgtcaaggtc a tcaaaaata     1320 agaaaagtct gaggaactgt caaaactaag aggaacccaa ggagacatga g aattatatg     1380 taatgtggca ttctgaatga gatcccagaa cagaaaaaga acagtagcta a aaaactaat     1440 gaaatataaa taaagtttga actttagttt tttttaaaaa agagtagcat t aacacggca     1500 aagtcatttt catattttc ttgaacatta agtacaagtc tataattaaa a atttttaa     1560 atgtagtctg gaacattgcc agaaacagaa gtacagcagc tatctgtgct g tcgcctaac     1620 tatccatagc tgattggtct aaaatgagat acatcaacgc tcctccatgt t ttttgtttt     1680 ctttttaaat gaaaaacttt attttttaag aggagtttca ggttcatagc a aaattgaga     1740 ggaaggtaca ttcaagctga ggaagttttc ctctattcct agtttactga g agattgcat     1800 catgaatggg tgttaaattt tgtcaaatgc tttttctgtg tctatcaata t gaccatgtg     1860 atttctcttct ttaacctgtt gatgggacaa attacgttaa ttgattttca a acgttgaac     1920 caccttaca tatctggaat aaattctact tggttgtggt gtatatttt t gatacattc     1980 ttggattctt tttgctaata ttttgttgaa aatgtttgta tctttgttca t gagagatat     2040 tggtctgttg ttttctttc ttgtaatgtc attttctagt tccggtatta a ggtaatgct     2100 ggcctagttg aatgatttag gaagtattcc ctctgcttct gtcttctgaa a gagattgta     2160 gaaagttgat acaattttt tttctttaaa tatcttgata gaattc                      2206
```

EPISOMALLY REPLICATING VECTOR, ITS PREPARATION AND USE

The present invention relates to stably episomally replicating vectors, comprising at least one scaffold/matrix attached region (S/MAR) and at least one viral or eukaryotic origin of replication (ORI), cells comprising these, processes for their preparation, and their use, in particular as a medicament or diagnostic.

At present, vectors are widely used in research and therapy. In this context, vectors are used in particular for transfecting or for transforming eu- and prokaryotic cells or cell systems and, in these, bringing effectors into action which code, for example, for pharmaceutically/medicinally relevant proteins or peptides, but also for proteins necessary for replicating the vectors themselves. Effectors are understood in general as meaning substances which produce a particular effect of metabolic or therapeutic nature in the host cell. Customary effectors are nucleic acids coding for proteins or peptides, ribozymes or antisense RNAs and antisense DNAs.

Vectors are of particular importance in gene therapy. The fundamental object of gene therapy is the introduction of nucleic acids into cells in order to express an effector gene. Three fundamental problems exist here in gene therapy, a) the introduction of the gene (gene delivery), b) the maintenance of the gene (gene maintenance) and c) the expression of the gene (gene expression). In this context, just the maintenance of the gene and thus the stable and persistent expression of genes is a basic condition for successful gene therapy, which until now has not been solved very satisfactorily. The prerequisite for this is therefore the use of suitable vectors. In this context, in gene therapy in-vitro and in-vivo processes are differentiated in principle. In in-vitro processes, cells are removed from the body and transfected ex vivo with vectors in order then to be introduced into the same or into another body again. In in-vivo gene therapy, vectors are administered systemically—e.g. via the blood stream. However, local application, in which a gene-therapy vector is applied locally in the tissue, for example in an affected section of vessel, is also possible (see, for example, WO 95/27070).

Thus, for the local application of a therapeutic gene in a selected case, for example, various strategies were developed based on modified balloon catheters, which are intended to permit direct administration of a substance or of a gene into the vascular wall. After a local administration using a double balloon catheter, Nabel, E. G. et al. (1990) Science, 249, 1285, for example, were able to detect a transient expression of the β-galactosidase gene in transfected cells of the femoral artery of the pig by means of liposomal and retroviral transfection.

Vectors are used in particular for the optimization of tissue-specific expression, which is used for the therapy of chronic diseases and hereditary diseases such as diabetes, hemophilia, ADA, muscular dystrophy, familial hypercholesterolemia or rheumatism, but can also be employed in acute diseases, such as vascular disorders—arteriosclerosis or its sequelae (stenosis, restenosis, cardiac infarcts)—and in tumors. Finally, the expression of genes and thus in particular the intracellular formation of therapeutic proteins and peptides, which on account of pathological or genetic modification are not or are no longer present to an adequate extent in the target organism, e.g. insulin or, in vascular cells, factor VII, etc., can also take place by means of a tissue-directed gene transfer.

An essential aim of somatic gene therapy is therefore to incorporate a therapeutic gene specifically into the target cells of the body after systemic or local administration and to express the therapeutic gene in these cells, without at the same time, however, inducing a transformation of the target cell or an immune response.

Up to now, there are two classes of vectors available for this: the viral vectors, where a differentiation has to be made here between a) episomally replicating vectors and b) vectors integrating into the DNA, and the nonviral vectors, in which c) a stable transfection is achieved by random insertion (integrating) or d) (transient) only a temporary transfection is present. The random integration into the host genome in approaches using integrating vectors can, depending on the integration point, lead both to insertion mutagenesis and to so called "silencing", in which no reading or expression of the inserted gene takes place. Transient expression vectors are limited in their life in terms of time, not stable and in some cases also subject to integration, but sometimes also transform the host cell. Their most important disadvantage, however, is that they often have to be repeatedly used on account of the limited expression associated with the short-lived nature. These vectors thus cause considerable problems just with respect to the effectiveness, reproducibility and safety necessary here.

The viral, episomally replicating vectors group does not have these disadvantages, as they are not integrated into the host genome and are retained in self-replicating form in the host cell. The term episomally replicating is understood here as meaning that the vector is not integrated into the genome of the host cell, but exists in parallel, is also replicated during the cell cycle and in the course of this the vector copies—depending on the number of the copies present before and after cell division—are distributed statistically in the resulting cells. Plasmid vectors, for example the pGFP-C1 vector (Clontech UK Ltd.), which have been optimized for research and other application purposes by alterations, are derived from the viral vectors. At present, only a few vectors are known which—starting from viral origins—replicate episomally in a few eukaryotic cells, e.g. SV40, BPV or EBV vectors. The replication origin of these vectors, however, requires interaction with one or more virally encoded trans-acting factors. These factors are also necessary for the stability of the vectors, but often lead to immortalization and transformation of the host cell or induce an immune response in the body (Ascenzioni et al. (1997) Cancer Letters 118, 135–142).

The eukaryotic virus SV40 (simian virus) thus replicates episomally in monkey cells and in some mammalian cells and cell lines. For this, the virus needs the so-called "large T antigen" for its existence in the host cell. The functions of the "large T antigen" are of crucial importance for the replication of the virus in the cell. The "large T antigen" binds, inter alia, to the viral DNA in the region of the origin of replication, and initiates its replication there (Mohr et al. (1987) EMBO J. 6, 153–160). Beside these activities which are important for the virus, the "large T antigen", however, also affects cellular functions. It is bound, inter alia, to proteins which are involved in the regulation of the cell cycle (cyclin, tubulin, cdc2). Infections with SV40 or transfections with vectors which carry genes coding for SV40 "large T antigen" can therefore lead to the immortalization of primary cells and induce tumor formation in animals (Fried, M. (1965) Proc. Natl. Acad. Sci. USA, 53, 486–491; Eckhart, W. (1969) Virology, 38, 120–125; Di Mayorca et al. (1969) Virology, 830, 126–133).

WO 98/27200 discloses a construct containing a human or mammalian replication origin cloned in a circular vector, which—without being integrated into the host genome— replicates episomally in human cells. Cossons N. et al. (1997) J. Cell. Biochem. 67, 439–450 describe vectors that contain a matrix attachment region (MAR) and different mammalian replication origin cloned in a circular vector. However, the episomal replication can only be maintained by selection pressure with selective antibiotics (G418) and even then occurs only with limited effectiveness. In fact, the stability per generation was only 80% under selective pressure. Therefore, no stable maintenance of the episomally replicating vector was observed. While the use of selective antibiotics like G418 is feasible for at least a limited maintenance in tissue culture experiments it is not applicable to an in vivo animal or human gene therapy approach because of the high toxicity of the used antibiotics.

The previously known vectors therefore on the whole have considerable disadvantages and are only of very limited suitability for gene transfer, in particular into mammalian cells. The object of the present invention was therefore to develop a vector which has the advantages of stably episomally replicating viral vectors, without being dependent on trans-acting viral factors or expression of viral protein, and thus essentially to avoid any type of cell transformation or immune response, and to achieve an improved maintenance of the gene compared with the prior art.

The present invention therefore relates to a stably episomally replicating vector which contains at least one scaffold/matrix attached region (S/MAR) and at least one viral or eukaryotic origin of replication (ORI).

Scaffold/matrix attached regions are understood as meaning sequences of nucleic acids which can subdivide chromatin in eukaryotic chromosomes in discrete domains, in particular in topologically connected so-called loop domains, and thus have crucial importance for structure and function, in particular, of the eukaryotic chromosome (Luderus, M. E. et al. (1994) Binding of matrix attachment regions to lamin polymers involves single-stranded regions and the minor groove, Mol. Cell Biol., 14, 6297–6305). These loop domains essentially contain all necessary cis-regulatory elements for the coordinated expression of the genes within a so-called "domain". The domains are limited by sequences which accumulate specifically on the nuclear matrix or the nuclear structure (scaffold). These sequences are called S/MARs and are usually several hundred base pairs long and rich in adenosine and thymidine (70%). Although cloned SAR and MAR elements have common structural properties, until now no consensus sequence has been identified (Boulikas, T. (1993) J. Cell. Biochem. 42, 14–22). S/MAR elements can increase the expression of heterologous genes after genomic integration (Klehr, D. et al. (1991) Biochem. 30, 1264–1270). S/MARs are credited with importance in the topological coiling of DNA (Bode, J. et al., (1992) Science 2555, 195–197). S/MAR elements can be isolated and identified, on the one hand, by the characterization of DNA bound in vivo to the nuclear matrix, on the other hand by the characterization of DNA fragments which can bind to DNA free nuclear matrix in vivo (Lewin, B. (1994) Genes V, Oxford University Press, 776–778; Mielke et al. (1990) Biochem. 29, 7475–7485). Examples of the identification and characterization are found in Bode J. et al., (1995) (Scaffold Matrix Attachment Regions (S/MAR): Structural properties creating transcriptionally active loci, Int. Rev. Cytol. 162A, 389ff., Academic Press, Orlando) and Bode J. et al. (1992; supra). From this and from the knowledge of the person skilled in the art, appropriate isolation possibilities result.

The expression "origin of replication" (ORI) is understood as meaning the general starting point or origin of replication in eukaryotic or prokaryotic cells and viruses. These ORIs support the replication and form the attachment points for various replicators.

Methods for the isolation of the ORI sequences from animal cells are known to the person skilled in the art and are described, for example, in a review article by DePamphilis, M. L. (1993) Annu. Rev. Biochem. 62, 29–63. Typical methods are, for example, "nascent strand extrusion" (Kaufmann, G. et al. (1985) Mol. Cell. Biol., 5, 721–727) or "anticruciform immunoaffinity purification" (Bell, D. et al. (1991) Biochem. Biophys. Acta, 1089, 299–308).

In consequence, it was completely surprising that a vector in which only one or more S/MAR elements are connected to one or more eukaryotic or viral ORIs is, on the one hand, not integrated into the genome, which would have normally been expected according to the prior art (Wegner et al. (1989) Nucleic Acids Research 17, 9909–9932), and is, on the other hand, stably episomally replicated without being dependent on in-trans-acting factors (of viral origin) for its replication. Since it has otherwise surprisingly also turned out that the vector according to the invention is stable and it is retained without selection by antibiotics for up to over approximately 100 generations, it is an advantageous vehicle for gene therapy, research and all sorts of other application areas. Stable episomal replication within the present invention means, that the vector is retained in the transfected cell over at least 30 generation, preferably over at least 50 generations, more preferably over at lest 80 generations, at least 100 generation or at least 200 generations without the ongoing application of selective pressure. A vector is considered to be successfully retained if it can still be detected by Southern blot analysis and/or only a small number of cells die in tissue culture after readdition of selective pressure (for instance G418). The vector according to the invention thus has, on the one hand, the advantage that the problems associated with random integration do not occur. On the other hand, as a result of the stable episomal replication a long-lasting action can be achieved, such that repeated treatment is not necessary, i.e. the problem of the gene retention in the transformed cell (gene maintenance) is essentially solved. Otherwise, without in-trans-acting factors (of viral origin) whose sequences are also already present in the host genome in many, just immortalized cells, transformation or immortalization of the host cell or induction of the immune response by viral proteins is not to be feared. The expression system is also based exclusively on chromosomal elements. The vector according to the invention therefore offers the necessary effectiveness, reproducibility and safety.

All in all, the vector components in general work together functionally such that the S/MAR allows stable episomal replication without the vector being integrated into the host genome or replication factors foreign to the cell having to be added to the ORIs for this. The S/MARs to this extent replace the replication factors or provide for activity of endogenous replication factors. The expansion of an ORI with S/MAR at least guarantees its functionability in plasmids.

In particular, the vector according to the invention can be an expression vector. The expression vectors have the advantage that they can express genes of very different types in the host cell. Expression vectors are understood as meaning vectors in which a gene coding for a peptide or protein is under the control of host-specific gene-regulatory sequences. Within the meaning of this invention, these are vectors which are suitable for the (episomal) expression of a gene and in addition to the corresponding gene sequence additionally also have promoter, operator and terminator sequences for the transcription and the sequence of the ribosomal binding sites for the translation. Straight expression vectors are very suitable for gene therapy or the in-vitro expression of various genes both in eukaryotes and in prokaryotes.

The vector according to the invention can otherwise also be distinguished in that it does not contain any nucleic acids coding for replication factors which act in trans. As mentioned above, particularly the in-trans-acting factors normally in vectors previously known from the prior art with viral ORI which was necessary for a replication of the information encoded on the vector are disadvantageous. The particular advantage of this embodiment is therefore that here these replication factors can be dispensed with, in particular those which show an action in trans and at the same time bring about, for example, a change in the host cell.

The expression replication factor within the meaning of this invention is understood generally as meaning factors which are necessary for the replication of the vector, that is, for example, bind to the ORIs and bring about a doubling of the nucleic acids. Such replication factors can be both proteins and peptides. The term trans action mentioned in this connection is broadly interpreted within the meaning of this invention. Trans action is any action of a replication factor which is not immediately directed at the relatively close environment of its sequence coding for it. Examples of replication factors within the meaning of this invention would be the SV40 large T antigen, trans-activating factors such as EBNA1 from EBV vectors and E1 and E2 of the BPV vectors.

In a further embodiment, the vector does not contain any nucleic acids coding for replication factors—in particular also those of viral origin—completely independent of whether they act in-trans or not. This is possible, since here there is no longer any functional dependence on viral replication factors and the danger of the transformation is also better excluded.

A vector is particularly preferred which does not contain any nucleic acid coding for viral proteins at all. The advantage of this embodiment is that no viral proteins whatsoever are expressed any longer and thus the otherwise frequently occurring induction of the immune response is completely suppressed, which makes this embodiment very particularly suitable for therapy. An example of a viral protein which is simultaneously a replication factor and acts in-trans is the known "large T antigen" of the SV40 virus, which is known for its tumor-inducing or immortalizing action.

The present invention further relates to a vector in which the "origin of replication (ORI)" is used for propagation in eukaryotes, it preferably being selected from the group of the viral ORIs such as EBV-ORI, BPV-ORI or in particular SV40-ORI. Propagation in eukaryotes is used, in particular, in therapeutic applications and for research purposes in this field of application.

A vector according to the invention in which the ORI is used for propagation in prokaryotes, in this case preferably the pUC-ORI, likewise comes under the invention. A vector equipped in this way has the advantage that it can be utilized for the replication of the vector in prokaryotes and thus can be replicated comparatively simply in high yields.

In a particularly preferred embodiment of the vector, one or more "origins of replication" will be contained for propagation in eukaryotes and one or more for propagation in prokaryotes, preferably at least one for propagation in the eukaryote and at least one for propagation in the prokaryote.

The advantage of this embodiment is that, on the one hand, the vector can easily be replicated in prokaryotes and, on the other hand, the same vector can be stably maintained in eukaryotes.

Vectors according to the invention are also those wherein the S/MAR originates from a mammal and is preferably even of human origin. The advantage of this embodiment is that particularly good propagation in eukaryotes can be achieved thereby, in particular in the course of gene therapy. A particularly preferred S/MAR in that respect is selected from the 5' region of the interferon β gene of human origin, isolated as the 2.0 kb EcoRI/BglII fragment from the plasmid pTZ-E20 (Bode et al. (1992) supra; FIG. 4).

Episomally replicating vectors can also additionally contain one or more genes mediating antibiotic resistance. These are used, in particular, for selection and for control, whether a successful transfection or transformation of the cells treated with the vector is present. In this case, genes which mediate a resistance against antibiotics selected from kanamycin, geneticin, gentamycin, ampicillin, tetracycline, streptomycin, spectinomycin, nalidixic acid, rifampicin, chloramphenicol and/or zeocin are particularly preferred, since these antibiotics known to the person skilled in the art are suitable for the selection, it being possible to add to these any others from his expert knowledge.

A particularly preferred embodiment of the vector contains the SV40 ORI and a scaffold/matrix attached region sequence from the 5' region of the interferon β gene, isolated as the 2.0 kb EcoRI/BglII fragment from the plasmid pTZ-E20 (Bode et al. (1992), supra; FIG. 4). Prokaryotic ORIs, such as the pUC ORI, genes mediating resistance, in particular against kanamycin, and various effectors can be added. A suitable starting vector which would be modified by the insertion of the various above mentioned regions to give a vector according to the invention would be the pGFP-C1 vector of the company Clontech UK Ltd. (see FIG. 2).

In a further example, the vector according to the invention is distinguished in that it contains one or more promoter or activator sequences and/or one or more effectors.

Promoters are understood as meaning nucleic acid sequences which usually lie 5' from the sequence to be read and regulate the transcription rate of a gene. A differentiation is made here between activator and repressor sequences, which respectively increase or decrease the gene activity. "Enhancers" can be counted among the activators and differ from other regulation elements in that they usually lie at a greater distance from the promoter 5' or 3' and can increase the transcription activity in a position-independent manner, e.g. from human cytomegalovirus (EP 0 173 177), CMV immediate-early polypeptide (Pos. 216–809/Genbank Accession No.: K03104).

Particular groups of activator sequences and promoters which are also preferred here are constitutive, cell cycle-specific, tissue-specific, metabolically regulated and/or inducible promoters or activator sequences. On the whole, these have the advantage, depending on choice, of being appropriate to the cell situation, so that particular metabolic conditions or therapeutic needs of a cell can be taken into account or that the replication or expression can be controlled by external factors.

Preferred effectors code for certain substances, selected from proteins, peptides, ribozymes or antisense RNAs, or are antisense DNAs. Peptides are understood here as meaning a part of a protein, or an amino acid sequence, either of natural or synthetic type. The function of these effectors is extremely diverse and can be tailored to the particular therapeutic needs. In the widely diversified literature, many examples of this are available, coding sequences being known, in particular for therapeutic proteins. Without restricting the application possibilities of the vector according to the invention thereto, or this listing being intended to be complete, a few examples are mentioned here in which proteins, or genes coding for these proteins, can be used therapeutically in this connection: nitrogen monoxide synthase (see, for example, WO 95/27020), insulin (see, for example, EP-B 100 01 929), erythropoietin (see, for example, EP-B1-0 148 605), or blood clotting factors, such as, for example, factor VII, interferons, cytokines, hormones, growth factors etc. The choice of the suitable effectors employed in the vector remains left to the knowledge of the person skilled in the art.

A further subject of the present invention is also one or more cells which contain one or more of the vectors described above. Thus, embodiments of the invention are in particular described in which, for the storage or propagation of the vector, this is already included in a cell. Particularly preferred here are eu- or prokaryotic cells, in particular bacterial, yeast, insect, amphibian, fish or mammalian cells. In this case, it is, for example, also known in the case of fish cells that expression occurs after microinjection of foreign DNA (Winkler et al. (1991) Mol. Gen. Genet. 226, 129–140). Transgenic fish can likewise be produced (WO 96/03034; WO 96/32087; WO 98/15627).

Especially in gene therapy, nonimmortalized cells of human origin are preferred. The term "nonimmortalized" is to be understood in this connection as meaning that the cell is not transformed in the genome, i.e. not replicable at will, but is subject to the natural cell cycle and thus—in contrast to the tumor cell—is itself of limited life span and can only replicate within a limited framework (Alberts et al., Molecular Biology of the Cell: Cancer (1995) $3^{rd}$ Ed.).

A further embodiment of the invention is transgenic, preferably embryonic, stem cells, which contain the vector according to the invention and/or nucleic acids produced therefrom and, for example, allow the production of transgenic animals, as well as the transgenic animals themselves, in which some or all cells of the animal contain the vectors according to the invention, nucleic acids produced therefrom and/or, if appropriate, expression products or the genes (see WO 90/03432, WO 95/06716, EP 0 169 672, DE 196 32 532, WO 96/03034; WO 96/32087; WO 98/15627).

A further subject of the present invention is also a process for the preparation of a vector according to the invention, in which one or more scaffold/matrix attached regions are combined with at least one ORI. The best-known method for the preparation is the separation of a region from plasmids or other nucleic acids and the insertion or ligation into a vector, plasmid or other nucleic acid with the aid of restriction endonucleases (restriction enzymes).

A particular form of the process consists in replacing one or more of the nucleic acids coding for replication factors in the original vector by at least one S/MAR region. This is carried out by excising these regions by means of restriction enzymes and inserting the S/MAR fragment into the vector using the methods known to the person skilled in the art.

A further embodiment of the process consists in additionally inserting at least one ORI and/or a gene mediating antibiotic resistance. It is further necessary and useful in many application areas to insert into the vector at least one effector, preferably coding for a peptide or a protein. Recourse is made here to the techniques already addressed.

There are numerous applications for the vectors or cells according to the invention, for example the transfer of substances, in particular of pharmaceutically active compounds, especially for gene transfer. Gene transfer is used, for example, for the diagnosis or therapy of vascular and/or organ disorders. Gene therapy is of particular importance here. In this case, the genes integrated into the vectors are expressed in the target cell—for example by the action of an expression vector. This applies in particular to genes which code for pharmaceutically and medicinally relevant proteins. In particular, the episomally replicating vector according to the invention allows a particularly side effect-free use in the therapeutic respect and a particularly preferred use is that as a "shuttle vector" in gene therapy. A "shuttle vector" is understood as meaning a vector which can be propagated in at least two different cell types, or organisms, for example vectors which are first propagated or replicated in prokaryotes in order for, for example, eukaryotic cells then to be able to be transfected with these.

The in-vitro expression of one or more genes is likewise important as a use of the vector according to the invention or its cells. The vector thus makes possible a strong expression of genes and thus, for example, the preparation of proteins and peptides in large amounts in various cells and cell systems of both eukaryotic and prokaryotic type, without continuously placing the cells under selection pressure, which adversely effects both the protein yield and increases the process costs. Using the vector, it is also possible to express genes which code for proteins or peptides and which until now it has not yet been possible to express without difficulty—in particular in sensitive cell systems.

A further aspect of the invention is also the use of a vector according to the invention for the transfection of cells. Transfection is understood as meaning the inclusion of the vector in the cell. Thus, on the one hand, the transfection step necessary in gene therapy is meant, as well as the transformation of prokaryotic cells, for example for the propagation of the vector.

Otherwise, the invention also includes the use of the vectors according to the invention for the production of transgenic animals or stem cells, for example embryonic stem cells, since these vectors are suitable for use, in particular, in eukaryotic cells, and also for use for research purposes. Transgenic animals are to be understood as meaning those in whose cells the vectors according to the invention and, if appropriate, effectors propagated thereby are present. Transgenic stem cells are understood as meaning cells which are tranfected using the vectors according to the invention and from which, for example, transgenic animals can be produced or reared. Examples are disclosed in WO 96/03034, WO 96/32087, WO 98/15627, WO 90/03432, WO 95/06716, EP 169 672 and DE 19 632 532.

The invention in this case also includes as a further subject a composition which contains at least one of the vectors according to the invention and/or a cell which contains such a vector, and suitable additives and/or auxiliaries.

The suitable additives and auxiliaries are to be understood as meaning, in particular, adjuvants, stabilizers and/or transfection-facilitating substances. Also covered are transfection systems including transfection vectors, which are combined or associated with the vector according to the invention and its penetration into cells, which facilitate or even allow transfection or alternatively transformation. Auxiliaries are in particular to be understood as also meaning general protease inhibitors, such as PMSF, and nuclease inhibitors, such as EDTA.

Preferred transfection vectors are, for example, viral or nonviral vectors. It is further possible to use for the transfection other, nonviral, transfection-facilitating substances, for example those from a lipid, a polymer, a peptide or a porphyrin, also in combination with vectors.

Gene-therapy vectors can be obtained by complexing the vector according to the invention with liposomes (neutral or cationic). The vector is thus essentially included in the liposome, thus has a very high transfection efficiency (see, for example, WO 95/27070) and is essentially protected from DNAses. Transfection with nucleic acid-liposome complexes with the aid of Sendai viruses in the form of so-called HVJ liposomes (virosomes) is particularly advantageous, as by this means the transfection rate can be increased still further.

During lipofection, small unilamellar vesicles are prepared from cationic lipids by ultrasonic treatment of the liposome suspension. The vector is bound ionically to the surface of the liposomes, to be precise, for example, in such a ratio that a positive net charge remains and 100 percent of the vector is complexed by the liposomes. In addition to the lipid mixtures DOTMA (1,2dioleyloxylpropyl-3-trimethylammonium bromide) and DOPE (dioleylphosphatidylethanolamine) employed by Felgner et al. (Felgner, P. L. et al (1987) Proc. Natl. Acad. Sci. USA 84, 7413–7414), in the meantime numerous novel lipid formulations have been synthesized and tested for their efficiency on the transfection of various cells. Examples of the novel lipid formulations are DOTAP or DOGS. An example of the preparation of DNA-liposome complexes from phosphatidylcholine, phosphatidylserine and cholesterol and their successful use in the transfection of vascular walls with the aid of Sendai viruses is described in WO 95/27070.

It is particularly advantageous if the vector-liposome complex contains nucleic acid-binding proteins, for example chromosomal proteins, preferably HMG proteins (high mobility group proteins), in particular HMG1 or HMG2 or nucleosomal histones, such as H2A, H2B or H3 or H4, since by this means the expression of the gene integrated in the vector can be increased. The chromosomal proteins can be isolated, for example, from calf thymus or rat liver according to generally known processes or prepared by genetic engineering. Human HMG1 can, for example, be prepared particularly easily recombinantly by methods known to the person skilled in the art using the human cDNA sequence (Wenn, L. et al. (1989) Nucleic Acids Research 17(3), 1197–1214).

A histidine-containing polypeptide which increases membrane permeation can likewise be employed. A so-called polyfection solution, comprising a vector according to the invention with the desired effector, a fusion protein made from tissue-specific peptide and a DNA-forming portion, e.g. a positively charged domain, and a peptide which increases membrane permeation, is preferably employed. In addition, coupling of the vector to the liposomes by means of a, for example, introduced C-terminal cysteine to an activated lipid component is known.

A further subject of the present invention is a medicament or a diagnostic which comprises an episomally replicating vector having at least one scaffold/matrix attached region and at least one viral or eukaryotic origin of replication and/or one or more of these vector-containing cells and, if appropriate, suitable additives or auxiliaries (see above).

Another embodiment of the present invention also relates to a composition, for example in the form of a transfection system, comprising one or more vectors and/or cells comprising these vectors and a further substance, for example for the transfection of cells. The polyfection solution described above would be particularly preferred here.

The following figures and examples are intended to describe the invention in greater detail without restricting it:
Figures FIG. 1 shows a vector with the sketched regions present on this vector as an exemplary embodiment In this particularly preferred embodiment, the following sequence elements are found: an SV40 ORI (135 base pairs) for propagation in eukaryotes, a kanamycin resistance gene (1399 base pairs) for selection both in E.coli and in eukaryotes (mediates resistances to kanamycin or geneticin), a pUC-plasmid ORI (643 base pairs) for propagation in E.coli and a matrix attached region (from the 5' region of the human interferon β gene, 1984 base pairs) for propagation in eukaryotes.

On interaction of these elements with, for example, an effector element, by means of the cooperation of the matrix attached region, in particular with the SV40 ORI, an episomally replicating vector results whose transfection can be checked by the kanamycin resistance gene and which propagates in prokaryotes through the pUC-ORI and can thus be prepared in an adequate amount.

Figure 1:
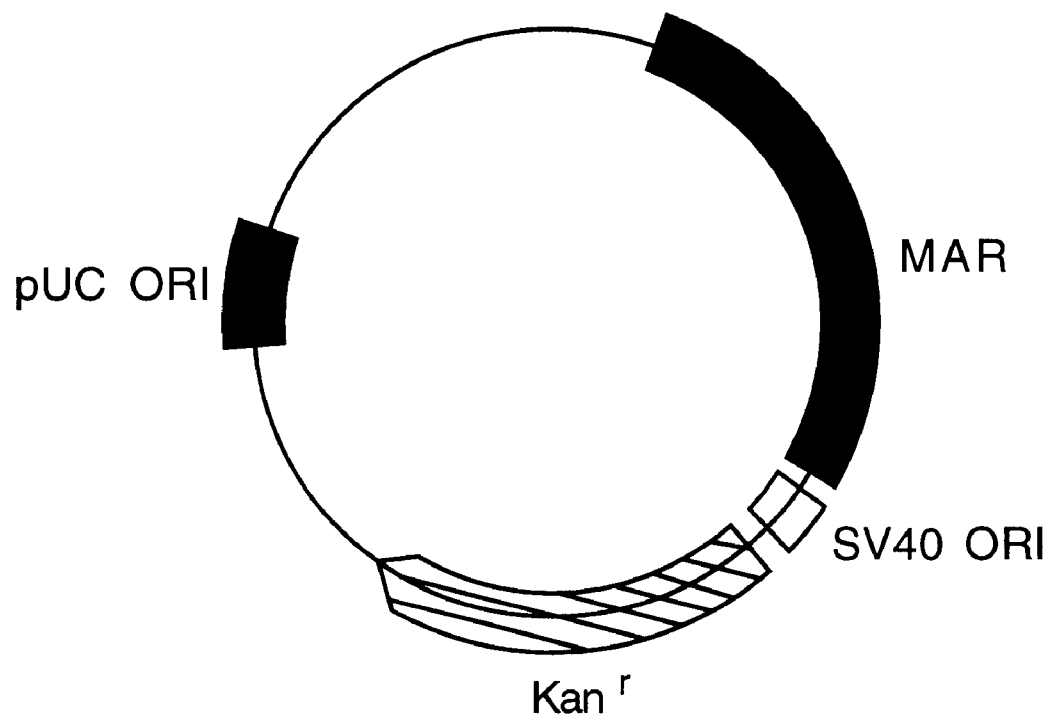
Figure 2:
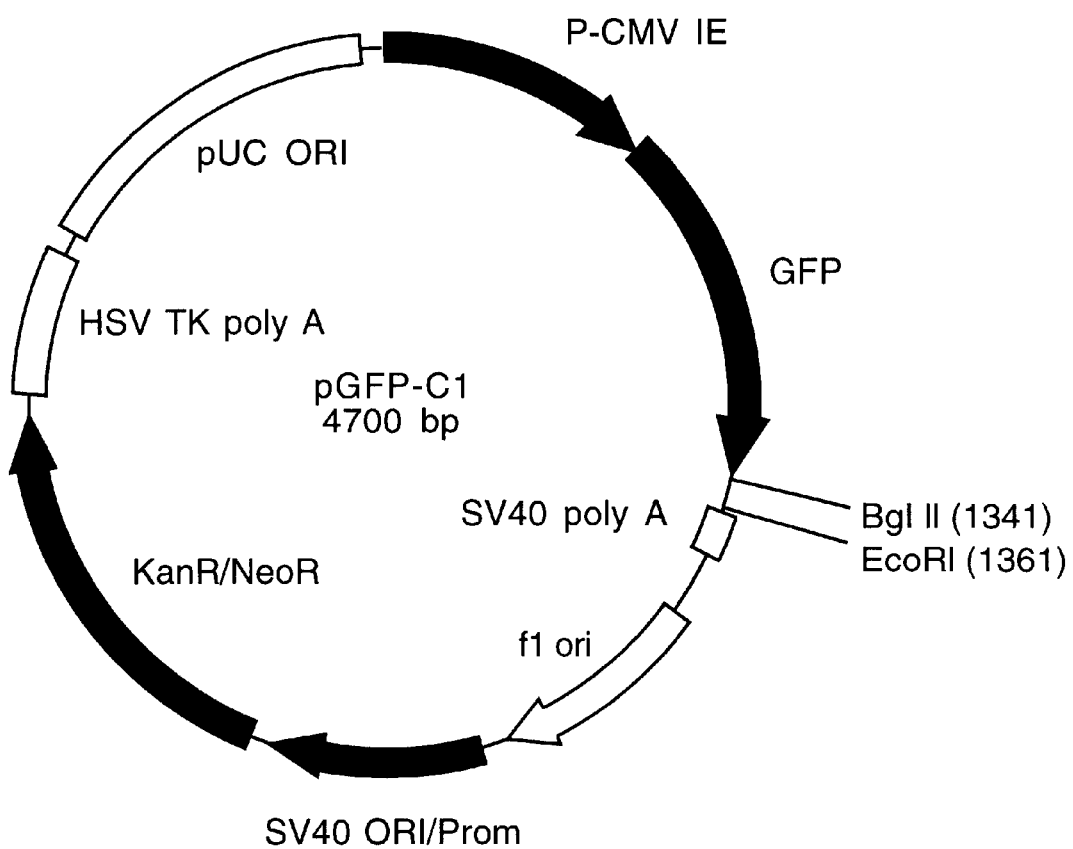
FIG. 2 shows the pGFP-C1 vector employed according to Examples 1 and 2, as was supplied by the company Clontech and which was used in the examples and a preferred preparation process.

According to Example 1, S/MAR was integrated here into a vector according to FIG. 2, so that a vector according to the invention results. This contains an (S/)MAR, a 2.0 kb EcoRI/BgIII fragment of the plasmid pTZ-E20 from the 5' region of the interferon β gene according to FIG. 4, the SV40 ORI, the pUC ORI, the resistance gene Kan/Neo with associated HSV TK poly A and promoter $P_{amp}$, the "enhancer" pCMV, the "SV40 early promoter" pSV40 and the GFP/green fluorescent protein. The results of Examples 1 to 5 have also been achieved using an appropriate vector.

Figure 4:
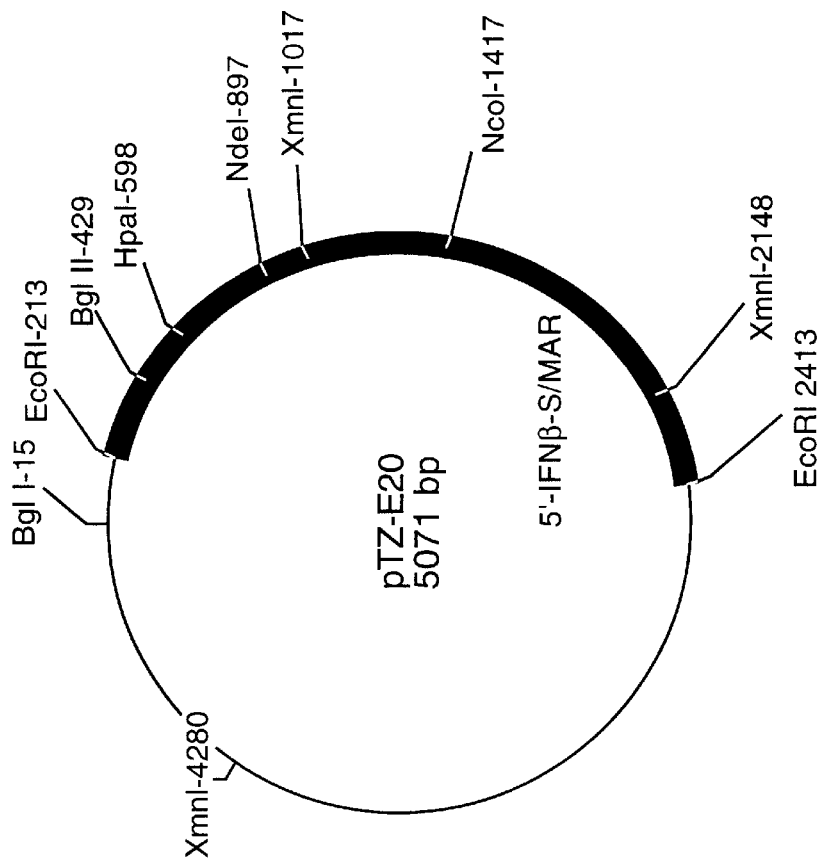

FIG. 4 shows the plasmid pTZ-E20.

SEQ ID NO: 1 shows the nucleic acid sequence of the human interferon β S/MAR.

EXAMPLES

Example 1

Preparation of a Preferred Episomally Replicating Vector

An S/MAR fragment from the 5' region of the human interferon β gene (SEQ ID NO: 1) was isolated from the plasmid pTZ-E20 (Bode, J. et al., loc. cit.) as 2.0 kb EcoRI/BgIII fragment and inserted into the polylinker PGFP-C1 (see FIG. 2). A vector according to the invention, designated as pEPI-1, resulted thereby. In another experiment, the gene coding for the SV40 "large T antigen" was excised from another viral/plasmid vector and replaced by S/MAR and a vector according to the invention was thus also obtained.

Example 2

Transfection and Selection of eu- and Prokaryotic Cells

Figure 3:
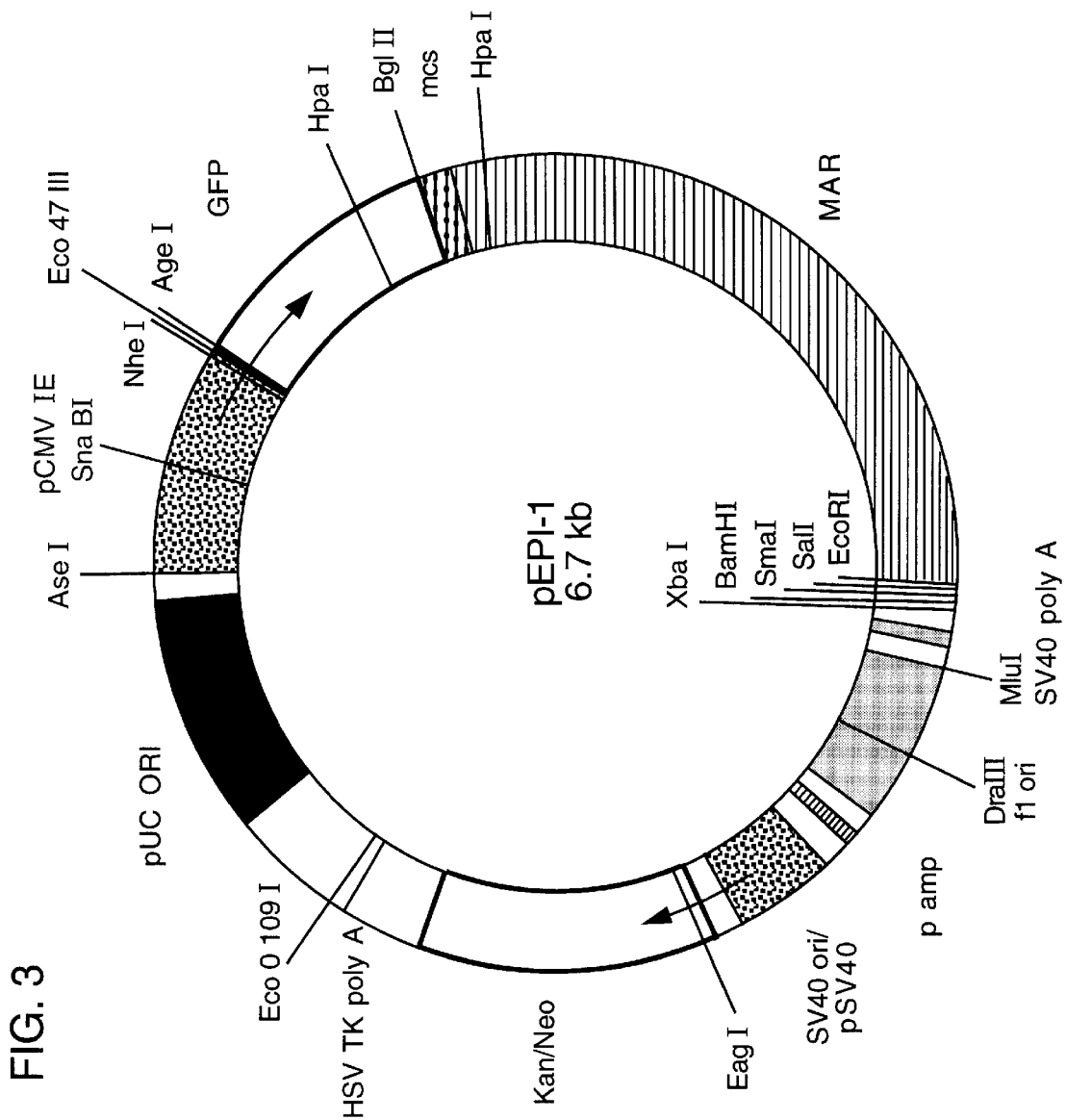
FIG. 3 shows a particular embodiment of the vector according to the invention, designated here as pEP I-1, using which some of the examples were carried out.

Chinese hamster ovary (CHO) cells were cultured in Ham's F12medium with 10% FCS, 2.5 µg/ml of amphotericin B and 50 µg/ml of gentamycin. $3\times10^6$ CHO cells were electroporated and incubated with 5 µg of the vector pEPI-1, prepared according to Example 1, (FIG. 3) or pGFP-C1 (FIG. 2). One day after the electroporation, transfected cells were selected by means of 500 µg/ml of G418, transfected cells surviving on account of their antibiotic resistance. After two weeks, stable clones were isolated and cultured with 250 µg/ml of G418. A similar procedure was used with E.coli cells.

Example 3
Retransfection

A HIRT extract (Hirt, B. (1967) J. Mol. Biol., 26, 365–369) obtained from the transfected CHO cells according to Example 2 was used in order to transfect new CHO cells according to the procedure in Example 2.

Example 4
Results of Investigations of the Cells According to Examples 1–3

After isolation of the DNA, digestion with restriction enzymes, blotting and hybridization experiments with a labeled pEPI-1 probe, it was found that random integration of the vector had not taken place in Example 2 and to be precise in any of the clones. The vector according to the invention, in this case pEPI-1, did not show any hybridization with the chromosomal DNA, while a HIRT extract obtained from cells according to Example 2 and Example 3 showed an isolated DNA with the restriction pattern identical to the vector according to the possible to detect the vector (see Example 3), as well as in E.coli cells. This contradicts the result known in the prior art, that in a highly amplified vector which has carried an AT-rich sequence of another type a head-to-tail integration takes place (Wegner et al. (1989) Nucleic Acids Research 17, 9909–9932). However, vectors which carry only a corresponding ORI or only S/MAR integrate randomly into the genome of the host (see also Klehr et al. (1992) Biochemistry, 31, 3222–3229, and Schübeler et al. (1996) Biochemistry, 35, 11160–11169). Thus, it is incidentally also demonstrated that CHO cells express no T antigen, since otherwise no integration of the vectors only carrying ORIs would take place. Furthermore, the results of a Southern analysis have also shown that the vectors according to the invention replicate efficiently and stably extrachromosomally; they are thus episomal vectors, about 20 copies of the vector being present in each clone.

Example 5
Stability and Expression Investigations

In order to investigate the plasmid stability and the expression of the neomycin resistance gene, transfected CHO cells according to Example 2 were cultured for more than 2 months (at least 100 generations) in a medium according to Example 2, but without addition of G418 and therefore without selection pressure by antibiotics.

If at different times during the entire culturing period some of the cultured G418 cells were added to the medium, only an insignificant number died in each case. It was also possible by means of Southern analysis to detect the episomal vector separately at any time.

It can be concluded, however, from this that on the one hand the vector is stable in CHO cells even without selection over at least 100 generations and on the other hand also the kanamycin resistance, and thus a nucleic acid sequence inserted in the vector in the form of an effector, is expressed in each generation.

Example 6
Propagation of the Vector in Human Cells

HaCat cells (human skin keratinocytes) were cultured in DMEM (Dulbecco's modified Eagle Medium) with 10% FCS. The HaCat cells were—in the same manner and under the same conditions as described in example 2—transfected with vector pEPI-1 prepared according to example 1 and selected 4 weeks after the beginning of the selection stable clones were isolated and cultured with 250 μg/ml of G418.

Example 7
Results of Investigations of the Cells According to Example 6

The DNA of 6 clones according to example 6 was isolated. A Southern analysis as described in example 4 was conducted and in a further experiment the whole vector was amplificated by PCR. Two primers in opposite facing were selected from the Neo Gene (neo-fwd and neo-up), resulting in only circular molecules being amplificated. Both experiments showed that the vectors according to the invention replicate efficiently and stably extrachromosomally; they are thus episomal vectors, about 20 copies of the vector being present in each clone. The Neomycin-cassette was efficiently expressed.

The results show that vectors according to the invention can be propagated and expressed episomally in human cells as well.

We claim:

1. A stably episomally replicating vector wherein said vector is retained for over at least 30 generations of cell divisions without the ongoing application of selective pressure, comprising a nucleic acid sequence encoding at least one scaffold/matrix attached region (S/MAR) originating from the 5' region of the interferon β gene and at least one SV40 or BPV origin of replication (ORI).

2. The vector of claim 1, wherein said vector is an expression vector.

3. The vector of claim 2, wherein said expression vector comprises a nucleic acid encoding a nitrogen monoxide synthase, insulin, erythropoietin, blood clotting factor, interferon, cytokine, hormone, or growth factor.

4. The vector of claim 1, wherein said vector is retained in episomal form for over at least 50 generations of cell divisions without the ongoing application of selective pressure.

5. The vector of claim 1, wherein said vector is retained in episomal form for over at least 80 generations of cell divisions without the ongoing application of selective pressure.

6. The vector of claim 1, wherein said vector is retained in episomal form for over at least 100 generations of cell divisions without the ongoing application of selective pressure.

7. The vector of claim 1, wherein said vector is retained in episomal form for over at least 200 generations of cell divisions without the ongoing application of selective pressure.

8. The vector of claim 1, wherein said vector does not comprise a nucleic acid encoding a viral protein.

9. The vector of claim 1, further comprising an ORI for propagation in a prokaryote that is the pUC ORI.

10. The vector of claim 1, comprising a 2.0 kb EcoRI/BglII fragment spanning nucleotides 217–2206 of SEQ ID No.1 encoding the S/MAR of the interferon β gene.

11. The vector of claim 1, wherein said vector further comprises at least one gene mediating antibiotic resistance.

12. The vector of claim 11, wherein said gene mediates resistance to an antibiotic selected from the group of antibiotics consisting of kanamycin, geneticin, gentamicin, ampicillin, tetracycline, streptomycin, spectinomycin, nalidixic acid, rifampicin, chloramphenicol, and zeocin.

13. The vector of claim 1, wherein said vector further comprises a promoter selected from the group of promoters consisting of constitutive promoters, cell cycle-specific promoters, tissue-specific promoters, metabolically regulated promoters, and inducible promoters.

14. The vector of claim 1, wherein said vector further comprises an activator sequence selected from the group consisting of constitutive activators, cell cycle-specific activators, tissue-specific activators, metabolically regulated activators, and inducible activators.

15. The vector of claim 1, wherein said vector further comprises a polynucleotide sequence encoding a substance selected from the group consisting of proteins, peptides, ribozymes, and antisense RNAs.

16. An isolated cell comprising the vector of claim 1.

17. The cell of claim 16, wherein said cell is a eukaryotic or prokaryotic cell and said vector contains one or more ORIs for propagation in a eukaryote and for propagation in a prokaryote.

18. The cell of claim 17, wherein said cell is selected from the group of cells consisting of a bacterial, yeast, insect, amphibian, fish, and mammalian cell, and wherein said vector contains at least one ORI for propagation in a eukaryote and at least one ORI for propagation in a prokaryote.

19. The cell of claim 17, wherein said cell is a nonimmortalized cell of human origin and said vector contains at least one ORI for propagation in a eukaryote and at least one ORI for propagation in a prokaryote.

20. A process for the preparation of a vector of claim 1, comprising the step of inserting one or more S/MARs into a vector comprising at least one SV40 or BPV ORI and lacking a nucleic acid encoding an SV40 T antigen.

21. The process of claim 20, wherein at least one ORI or a gene mediating antibiotic resistance is further inserted into said vector.

22. The process of claim 20, wherein a nucleic acid encoding at least one peptide or protein is further inserted into said vector.

23. A process for the preparation of a vector of claim 1, comprising replacing one or more nucleic acids encoding an SV40 T antigen in said vector by at least one S/MAR.

24. A process for transfecting a cell, said process comprising contacting said cell with a vector of claim 1.

25. A process for expressing a gene, comprising:
(a) providing a cell comprising a stably episomally replicating vector of claim 1, said vector further comprising a gene encoding a substance selected from the group consisting of nonviral peptides, proteins, ribozymes, and antisense RNAs; and
(b) culturing said cell under conditions suitable for expression of said gene.

26. A composition comprising either the vector of claim 1 or the cell of claim 16, and a transfection system selected from the group of transfection systems consisting of those which comprise a lipid, a polymer, a peptide, or a porphyrin.

* * * * *